United States Patent
Ding et al.

(10) Patent No.: US 7,318,936 B2
(45) Date of Patent: Jan. 15, 2008

(54) MINIMIZATION OF DRUG OXIDATION IN DRUG IRRADIATED EXCIPIENTS FORMULATIONS

(75) Inventors: Zhongli Ding, Sunnyvale, CA (US); Lothar Walter Kleiner, Los Altos, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 10/986,922

(22) Filed: Nov. 12, 2004

(65) Prior Publication Data

US 2005/0158379 A1 Jul. 21, 2005

Related U.S. Application Data

(60) Provisional application No. 60/519,981, filed on Nov. 14, 2003.

(51) Int. Cl.
*A61K 9/20* (2006.01)
*A61L 2/08* (2006.01)

(52) U.S. Cl. .............. 424/476; 424/465; 424/400; 514/2; 422/20; 422/21; 422/22

(58) Field of Classification Search ........... 424/465, 424/476, 400; 514/2; 422/20–22
See application file for complete search history.

(56) References Cited

U.S. PATENT DOCUMENTS

| | | | | |
|---|---|---|---|---|
| 4,026,705 A | * | 5/1977 | Crivello et al. | 430/280.1 |
| 4,156,067 A | | 5/1979 | Gould | 582/73 |
| 4,347,737 A | * | 9/1982 | Beach | 73/159 |
| 4,692,446 A | * | 9/1987 | Erhardt et al. | 514/237.5 |
| 4,708,949 A | * | 11/1987 | Liu | 514/26 |
| 4,709,048 A | * | 11/1987 | Mobilio et al. | 548/439 |
| 4,717,713 A | * | 1/1988 | Zatz et al. | 514/2 |
| 5,073,268 A | * | 12/1991 | Saito et al. | 210/638 |
| 5,169,762 A | * | 12/1992 | Gray et al. | 435/69.1 |
| 5,424,471 A | | 6/1995 | Kennedy et al. | 558/146 |
| 5,587,149 A | * | 12/1996 | Punto et al. | 424/59 |
| 5,662,732 A | * | 9/1997 | Kelley et al. | 106/271 |
| 6,423,351 B2 | | 7/2002 | Wang | |
| 6,531,150 B1 | * | 3/2003 | Sunohara et al. | 424/463 |
| 2003/0091646 A1 | | 5/2003 | Gen | 424/486 |
| 2003/0180364 A1 | | 9/2003 | Chen et al. | |

FOREIGN PATENT DOCUMENTS

| | | |
|---|---|---|
| EP | 0 815 881 A2 | 1/1998 |
| JP | 2000-186032 | 7/2000 |
| WO | WO 98/23639 A2 | 6/1998 |

OTHER PUBLICATIONS

Calis, Sema, Farmaco 57(1), 55-62, 2002.*
Koseoglu, R., Applied Radiation and Isotopes 58(1), 63-68, 2003.*
Sintzel, Martina B., Drug Development and Industrial Pharmacy 23(9), 857-878, 1997.*
Polat, M., International Journal of Pharmaceutics 244(1-2), 169-179, 2002.*
Chahine, M. H. (Grasas y Aceites (Sevilla, Spain) 30(1), 25-30, 1979).*
Morehouse, Kim M. (Radiation Physics and Chemistry 42(1-3), 359-62, 1993).*
Sattar, Abdus (Journal of the American Oil Chemists' Society 53(7), 473-7, 1976).*
Tsao, Constance S. (Medical Science Research 24(7), 473-475, 1996).*
Brett J. (J Illum. Eng. Soc. 9(4) p. 197-204, 1980).*
Estes, Zane E. (Military Medicine 135(4), 296-9, 1970).*
Manthey, M. K., (Biochim Biophys Acta 1034, 207-212, 1990).*
Okide, G. B. (Bollettino Chimico Farmaceutico 137(7), 277-280, 1998).*

* cited by examiner

*Primary Examiner*—David Lukton
(74) *Attorney, Agent, or Firm*—Woodcock Washburn LLP

(57) ABSTRACT

This invention relates to compositions and methods for preventing oxidation of beneficial agents.

25 Claims, 1 Drawing Sheet

MINIMIZATION OF DRUG OXIDATION IN DRUG IRRADIATED EXCIPIENTS FORMULATIONS

CROSS-REFERENCE TO RELATED APPLICATIONS

This application claims benefit of U.S. provisional patent application No. 60/519,981, filed Nov. 14, 2003, which is incorporated herein by reference.

FIELD OF INVENTION

This invention relates to compositions and methods for preventing oxidation of beneficial agents.

BACKGROUND

Many excipients are sterilized by exposure to radiation before use in beneficial agent formulations. In certain types of excipients, including stearic acid and fatty acids, such irradiation produces free radicals, and peroxides. In the presence of beneficial agents which are susceptible to oxidation, such as amino acid sequences, lipids, DNA, and certain drugs, these free radicals and peroxides can oxidize the beneficial agents, thereby reducing the efficacy of the beneficial agent.

For example, when contacted by free radicals and peroxides, peptides and proteins are subject to a wide range of undesirable effects, such as sulfur oxidation, deleterious effects on carbonyls, crosslinking, hydroperoxy derivative formation, deamination, chloroamine formation, interconversions (i.e., His to Asn, Pro to HO-Pro), adduct formation (lipid peroxidation, amino acid oxidation, glycoxidation), aggregation, and peptide bond cleavage. This can lead to loss of activity, function, abnormal cellular uptake, modified gene transcription, or increased immunogenicity.

In the past, antioxidants and other free radical scavengers have been added to prevent undesirable reactions. For example, U.S. Pat. No. 6,423,351 discloses prevention of drug oxidation using a ferrous ion source. Antioxidants commonly employed in beneficial agent formulations include vitamin E, vitamin C, butylated hydroxytoluene, and butylated hydroxyanisole. However, this strategy has not always proved successful, and in all instances increases materials' costs for manufacturing the formulations.

It has now been discovered that introduction of an annealing step into the creation of drug formulations eliminates the need for scavengers, thus reducing the number of materials required to manufacture the formulations, and creating new compositions and methods for preventing oxidation of beneficial agents. Moreover, the present invention allows for protection from oxidation of beneficial agents in situations where the use of scavengers would be unsuitable.

SUMMARY

The present invention describes formulations for preventing oxidation of beneficial agents comprising beneficial agents, and excipients, wherein the excipients have been irradiated and annealed.

Methods of preventing oxidation of beneficial agents in the presence of irradiated excipients are described, the methods comprising annealing the excipients before combination with the beneficial agents.

DETAILED DESCRIPTION

Figure 1:
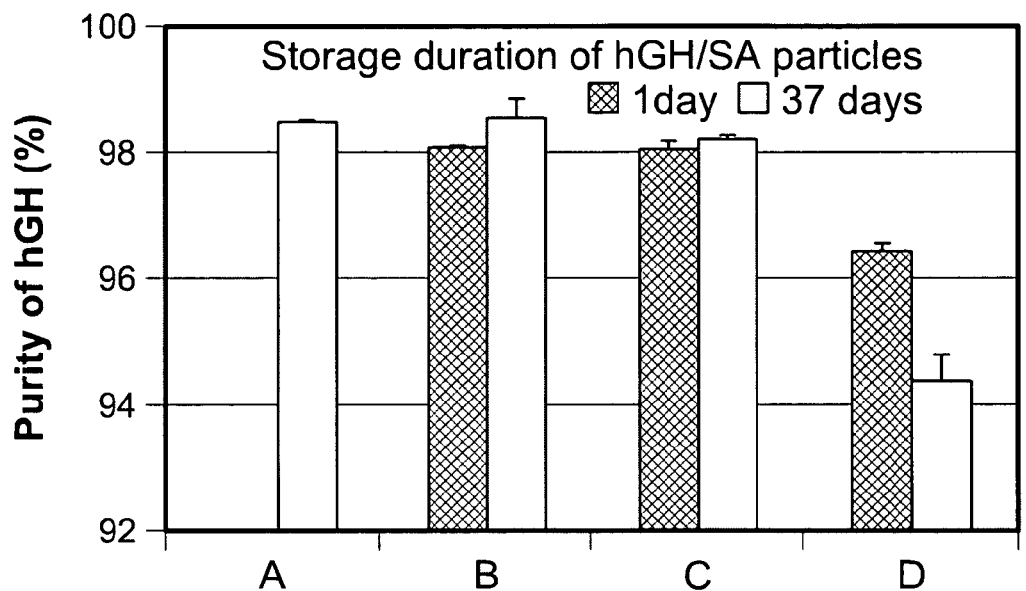
FIG. 1 is a graph comparing oxidation for several samples, including a composition of the present invention.

The present invention describes formulations for preventing oxidation of beneficial agents comprising beneficial agents, and excipients, wherein the excipients have been irradiated and annealed.

In general, the excipients include any excipients where irradiation of the compound would cause free radicals or peroxides to develop. The excipient may be irradiated in any conventional manner. The preferred excipients include stearic acid, other fatty acids, natural polymers, for example polysaccharides, or synthetic polymers, such as polyethylene glycol, polyvinylpyrrolidone, and polyvinyl alcohol. It is understood that the term "natural polymer" includes natural polymers that have been subsequently modified. Preferably, the fatty acids include palmitic acid, stearic acid, and $C_{20-22}$ fatty acids.

Annealing comprises heating the excipient to a temperature range above its melting point. While not wishing to be bound to a particular theory, it is believed that disturbing the crystal structure of the excipient hastens the decay of the free radicals.

Stearic acid has a melting point of about 69.7° C. When stearic acid is the excipient, the excipient is heated to a temperature in a range of about 70° C. to about 250° C. and then cooled. Preferably, the step of annealing comprises heating the excipient to a temperature range of about 70° C. to about 150° C. and then cooling the excipient. More preferably, the step of annealing comprises heating the excipient to a temperature of about 90° C. and then cooling the excipient.

The excipient may be annealed under vacuum. In another embodiment, the excipient is annealed under a nitrogen, helium, or argon atmosphere.

The excipient is either cooled by exposing the excipient to room temperature or by icing.

Other excipients, such as sucrose, buffers, and salts may be included in the formulation.

The beneficial agent is selected from the group consisting of a protein, a peptide, a lipid, a DNA sequence, an RNA sequence, a drug, or combinations thereof.

The amino acids residues cystein, methionine, tyrosine, tryptophan, phenylalanine, valine, leucine, histidine, glutamic acid, proline, threonine, arginine, and lysine are well known to be susceptible to oxidation. For example, cystein can form disulfides. Methionine can form a sulfoxide. Tyrosine, tryptophan, phenylalanine can be substituted, for example nitrotyrosine, hydroxytryptophan, and hydroxyphenylalanine. Valine and leucine can form hydroperoxides. Histidine can be converted to asparagines or aspartate. Glutamic acid can form oxalic acid. Proline can form pyrrolidone. Threonine can form 2-amino-3-ketobutyric acid. Arginine and lysine can form chloramines.

Preferably, the protein is human growth hormone, lysozyme, interferon alpha-2a, interferon alpha-2b, EPO, methionine-human growth hormone, des-phenylalanine human growth hormone, consensus interferon, albumin, omega-interferon, immunoglobulins, interleukines, G-CSF, GM-CG, TNF hot shock proteins, and combinations thereof. Preferably, the peptide is ShK-Dap22 (as disclosed in WO 9823639).

Drugs that can benefit from the present invention include all those known to be susceptible to oxidation. Such drugs may include amino groups, thiol groups, aldehyde groups, benzyl groups, hydroxyl groups, or unsaturated bonds. Preferably these drugs are epinephrine, theophyllin, risperidone, captopril, chlorpromazine, ergotamine, hydrocortisone, morphine, promethazine, and thiamine.

In one embodiment, the formulation further comprises a delivery platform.

In one embodiment, the delivery platform is a depot. This comprises a gel vehicle formulation comprising a bioerodible, biocompatible polymer and a solvent in an amount effective to plasticize the polymer and form a gel therewith, such as is described in U.S. patent application Ser. No. 10/295,603, filed Nov. 14, 2002, Publication No.2003/0180364, the entire disclosure of which is incorporated by reference herein as if reproduced in its entirety. The polymer is selected from the group consisting of: polylactides, polyglycolides, polyanhydrides, polyamines, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polyhydroxycellulose, polyphosphoesters, chitin, chitosan, gluronic acid, and copolymers, terpolymers and mixtures thereof.

In another embodiment, the delivery platform comprises microparticles, a polymeric matrix which encapsulates a mixture of excipient and beneficial agent. The matrix comprises a polymer selected from the group consisting of: polylactides, polyglycolides, polyanhydrides, polyamines, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polyhydroxycellulose, polyphosphoesters, chitin, chitosan, gluronic acid, and copolymers, terpolymers and mixtures thereof.

In another embodiment of the present invention, a method of preventing oxidation of a beneficial agent in the presence of an irradiated excipient comprising annealing the excipient before combination with the beneficial agent is described.

In general, the excipients include any excipients where irradiation of the compound would cause free radicals or peroxides to develop. The excipient may be irradiated in any conventional manner. The preferred excipients include stearic acid, other fatty acids, natural polymers, for example polysaccharides, or synthetic polymers, such as polyethylene glycol, polyvinylpyrrolidone, and polyvinyl alcohol. It is understood that the term "natural polymer" includes natural polymers that have been subsequently modified. Preferably, the fatty acids include palmitic acid, stearic acid, and $C_{20-22}$ fatty acids.

Annealing comprises heating the excipient to a temperature range above its melting point. While not wishing to be bound to a particular theory, it is believed that disturbing the crystal structure of the excipient hastens the decay of the free radicals.

Stearic acid has a melting point of about 69.7° C. When stearic acid is the excipient, the excipient is heated to a temperature in a range of about 70° C. to about 250° C. and then cooled. Preferably, the step of annealing comprises heating the excipient to a temperature range of about 70° C. to about 150° C. and then cooling the excipient. More preferably, the step of annealing comprises heating the excipient to a temperature of about 90° C. and then cooling the excipient.

The excipient may be annealed under vacuum. In another embodiment, the excipient is annealed under a nitrogen, helium, or argon atmosphere.

The excipient is either cooled by exposing the excipient to room temperature or by icing.

Other excipients, such as sucrose, buffers, and salts may be included in the formulation.

The beneficial agent is selected from the group consisting of a protein, a peptide, a lipid, a DNA sequence, an RNA sequence, a drug, or combinations thereof.

The amino acids residues cystein, methionine, tyrosine, tryptophan, phenylalanine, valine, leucine, histidine, glutamic acid, proline, threonine, arginine, and lysine are well known to be susceptible to oxidation. For example, cystein can form disulfides. Methionine can form a sulfoxide. Tyrosine, tryptophan, phenylalanine can be substituted, for example nitrotyrosine, hydroxytryptophan, and hydroxyphenylalanine. Valine and leucine can form hydroperoxides. Histidine can be converted to asparagines or aspartate. Glutamic acid can form oxalic acid. Proline can form pyrrolidone. Threonine can form 2-amino-3-ketobutyric acid. Arginine and lysine can form chloramines.

Preferably, the protein is human growth hormone, lysozyme, interferon alpha-2a, interferon alpha-2b, EPO, methionine-human growth hormone, des-phenylalanine human growth hormone, consensus interferon, albumin, omega-interferon, immunoglobulins, interleukines, G-CSF, GM-CG, TNFs hot shock proteins, and combinations thereof. Preferably, the peptide is ShK-Dap22 (as disclosed in WO 9823639).

Drugs that can benefit from the present invention include all those known to be susceptible to oxidation. Such drugs may include amino groups, thiol groups, aldehyde groups, benzyl groups, hydroxyl groups, or unsaturated bonds. Preferably these drugs are epinephrine, theophyllin, risperidone, captopril, chlorpromazine, ergotamine, hydrocortisone, morphine, promethazine, and thiamine.

In one embodiment, the formulation further comprises a delivery platform.

In one embodiment, the delivery platform is a depot. This comprises a gel vehicle formulation comprising a bioerodible, biocompatible polymer and a solvent in an amount effective to plasticize the polymer and form a gel therewith, such as is described in U.S. patent application Ser. No. 10/295,603, filed Nov. 14, 2002, Publication No. 2003/0180364, the entire disclosure of which is incorporated by reference herein as if reproduced in its entirety. The polymer is selected from the group consisting of: polylactides, polyglycolides, polyanhydrides, polyamines, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polyhydroxycellulose, polyphosphoesters, chitin, chitosan, gluronic acid, and copolymers, terpolymers and mixtures thereof.

In another embodiment, the delivery platform comprises microparticles, a polymeric matrix which encapsulates a mixture of excipient and beneficial agent. The matrix comprises a polymer selected from the group consisting of: polylactides, polyglycolides, polyanhydrides, polyamines, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polyhydroxycellulose, polyphosphoesters, chitin, chitosan, gluronic acid, and copolymers, terpolymers and mixtures thereof.

In one embodiment, the method further comprises compressing the mixture of the excipient with the beneficial agent to form a pellet, and then may further comprise grinding the pellet to form a ground pellet.

In the depot delivery embodiment, the method may further comprise adding the ground pellet to a viscous gel formulation comprising a bioerodible, biocompatible polymer and a solvent in an amount effective to plasticize the polymer and form a gel therewith, wherein the polymer is selected from the group consisting of: polylactides, polyglycolides, polyanhydrides, polyamines, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polyhydroxycellulose, polyphosphoesters, chitin, chitosan, gluronic acid, and copolymers, terpolymers and mixtures thereof.

Alternatively, in the microparticle delivery embodiment, the method may further comprise suspending the ground pellet in a bioerodible, biocompatible polymer matrix and encapsulating particles of the ground pellet, wherein the matrix comprises a polymer selected from the group consisting of: polylactides, polyglycolides, polyanhydrides, polyamines, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polyhydroxycellulose, polyphosphoesters, chitin, chitosan, gluronic acid, and copolymers, terpolymers and mixtures thereof.

Generally, beneficial agents may be administered to a patient by any known method in dosages ranging from about 0.001 to about 1.0 mmoles per kg body weight (and all combinations and subcombinations of dosage ranges and specific dosages therein). The useful dosage to be administered and the particular mode of administration will vary depending upon such factors as age, weight, and problem to be treated, as well as the particular beneficial agent used, as will be readily apparent to those skilled in the art. Typically, dosage is administered at lower levels and increased until the desirable diagnostic effect is achieved.

The present invention is further described in the following examples.

EXAMPLES

Example 1

Four samples, A, B, C, and D were prepared.

Sample A comprised lyophilized human growth hormone ("hGH").

Sample B comprised hGH mixed with stearic acid. The stearic acid was ground in nitrogen filled dry box and then mixed with hGH. This mixture was compressed into a pellet and ground again.

Sample C comprised hGH mixed with irradiated and annealed stearic acid. Stearic acid was sealed in a nitrogen filled container and γ-irradiated. The sealed stearic acid was incubated at the temperature range of 70-150° C. for 5-60 minutes, and then cooled to room temperature. The stearic acid was ground in nitrogen filled dry box and then mixed with hGH. This mixture was compressed into a pellet and ground again.

Sample D comprised hGH mixed with irradiated stearic acid. Stearic acid was sealed in a nitrogen filled container and γ-irradiated. The stearic acid was ground in a nitrogen filled dry box and then mixed with hGH. This mixture was compressed into a pellet and ground again.

The degree of oxidation of hGH was analyzed using a reverse phase HPLC for samples B, C, and D on the first day, and for all four samples 37 days later. The results are shown in FIG. 1. Sample D showed the deleterious effect that irradiation of stearic acid has on oxidizable compounds. As excipients are typically sterilized by exposure to radiation before use in beneficial agent formulations, a formulation like Sample B is not practical. However, Sample C showed that the present invention prevents oxidation when irradiated stearic acid is used.

Example 2

Stearic acid was sealed in a nitrogen filled container and γ-irradiated. Samples of the sealed stearic acid were incubated at 60° C., 75° C., and 90° C. for 10 min, 30 min, or 60 min, and then cooled to room temperature. The peroxide concentrations after these annealing steps were measured using conventional methods and the results are shown in TABLE 1.

A control sample of non-irradiated stearic acid had a peroxide concentration of 3.25 mEq/kg.

Stearic acid that was sealed in a nitrogen filled container and γ-irradiated had a peroxide concentration of 7.31 mEq/kg prior to annealing.

TABLE 1

| Time | Concentration at 60° C. (mEq/kg) | Concentration at 75° C. (mEq/kg) | Concentration at 90° C. (mEq/kg) |
|---|---|---|---|
| 10 min | — | 2.60 | 2.10 |
| 30 min | 5.87 | 2.49 | — |
| 60 min | 6.07 | — | 2.12 |

Example 3

Stearic acid was sealed in a nitrogen filled container and γ-irradiated. Samples of the sealed stearic acid were incubated at 60° C., 75° C., and 90° C. for 10 min, 30 min, or 60 min, and then cooled to room temperature. The relative free radical concentrations after these annealing steps were measured using conventional methods (nitrogen atmosphere, room temperature, 20 kGy) and the results are shown in TABLE 2. A control sample of non-irradiated stearic acid was used as the standard, and the differences reported in arbitrary units relative to the standard.

TABLE 2

| Time | Relative Units at 60° C. | Relative Units at 75° C. | Relative Units at 90° C. |
|---|---|---|---|
| 10 min | — | 1.5 | 0 |
| 30 min | 2193 | 0 | — |
| 60 min | 910 | — | 0 |

Thus, Table 2 shows that free radicals are eliminated in the stearic acid that was annealed above 75° C.

Example 4

Three samples, A, B, and C were prepared.

Sample A comprised lyophilized lysozyme ("lysozyme") mixed with stearic acid. The stearic acid was ground in nitrogen filled dry box and then mixed with lysozyme. This mixture was compressed into a pellet and ground again. The particles were then stored at 4° C. for one week.

Sample B comprised lysozyme mixed with irradiated and annealed stearic acid. Stearic acid was sealed in a nitrogen filled container and γ-irradiated. The sealed stearic acid was incubated at 70° C. for 60 minutes, and then cooled to room temperature. The stearic acid was ground in nitrogen filled dry box and then mixed with lysozyme. This mixture was compressed into a pellet and ground again. The particles were then stored at 4° C. for one week.

Sample C comprised lysozyme mixed with irradiated stearic acid. Stearic acid was sealed in a nitrogen filled container and γ-irradiated. The stearic acid was ground in nitrogen filled dry box and then mixed with lysozyme. This mixture was compressed into a pellet and ground again. The particles were then stored at 4° C. for one week.

Figure 2:
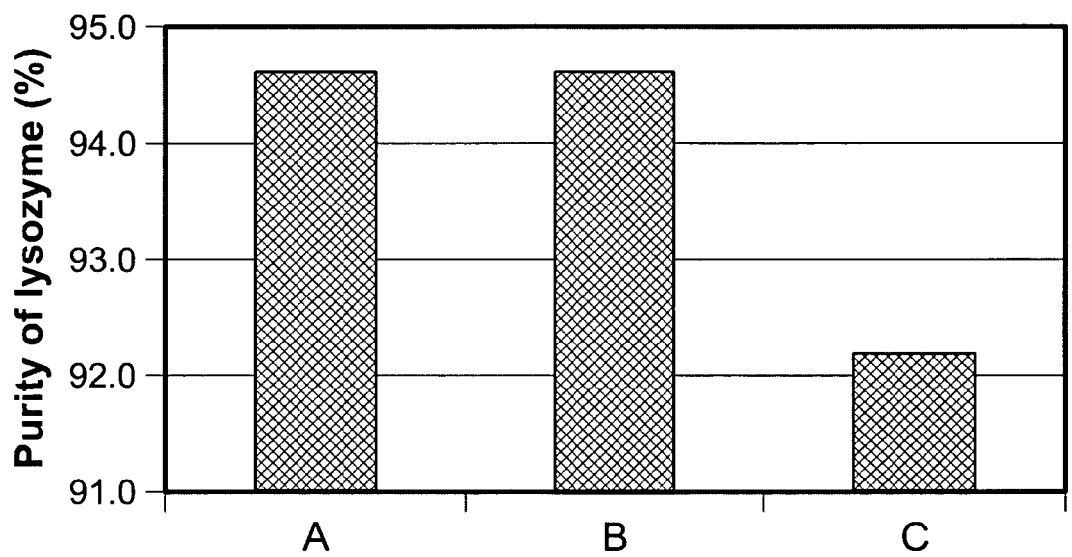
FIG. 2 is a graph comparing oxidation for several samples, including a composition of the present invention.

The degree of oxidation of lysozyme was analyzed using a reverse phase HPLC after the aforementioned one week. The results are shown in FIG. 2. Sample C showed the deleterious effect that irradiation of stearic acid has on oxidizable compounds. As excipients are typically sterilized by exposure to radiation before use in beneficial agent formulations, a formulation like Sample A is not practical. However, Sample B showed that the present invention prevents oxidation when irradiated stearic acid is used.

The disclosures of each patent, patent application, and publication cited or described in this document are hereby incorporated herein by reference, in their entireties.

Each recited range includes all combinations and subcombinations of ranges, as well as specific numerals contained therein.

Various modifications of the invention, in addition to those described herein, will be apparent to those skilled in the art from the foregoing description. Such modifications are also intended to fall within the scope of the appended claims.

What is claimed:

1. A method of inhibiting oxidation of a beneficial agent in the presence of an excipient that has been irradiated under conditions sufficient to form free radicals or peroxides comprising:
   annealing the excipient before combination with the beneficial agent; and
   combining the annealed excipient with the beneficial agent;
   wherein the excipient is a solid prior to annealing.

2. The method of claim 1 wherein the step of annealing comprises heating the excipient to a temperature range above its melting point and then cooling the excipient.

3. The method of claim 1 wherein the excipient is annealed under vacuum.

4. The method of claim 1 wherein the excipient is annealed under a nitrogen atmosphere.

5. The method of claim 1 wherein the excipient is annealed under a helium atmosphere.

6. The method of claim 1 wherein the excipient is annealed under an argon atmosphere.

7. The method of claim 2 wherein the excipient is cooled by exposing the excipient to room temperature.

8. The method of claim 1 wherein the excipient comprises stearic acid.

9. The method of claim 1 wherein the excipient comprises a fatty acid.

10. The method of claim 1 wherein the excipient is palmitic acid, stearic acid, or $C_{20-22}$ fatty acids.

11. The method of claim 1 wherein the excipient comprises a natural polymer.

12. The method of claim 11 wherein the excipient comprises polysaccharides.

13. The method of claim 1 wherein the excipient comprises a synthetic polymer.

14. The method of claim 1 wherein the excipient comprises a polymer selected from the group of polyethylene glycol, polyvinylpyrrolidone, and polyvinyl alcohol.

15. The method of claim 1 wherein the beneficial agent is selected from the group consisting of a protein, a peptide, a lipid, a DNA sequence, an RNA sequence, a drug, and combinations thereof.

16. The method of claim 15 wherein the beneficial agent is a protein selected from the group consisting of human growth hormone, lysozyme, interferon alpha-2a, interferon alpha-2b, EPO, methionine-human growth hormone, desphenylalanine human growth hormone, consensus interferon, albumin, omega-interferon, immunoglobulins, interleukins, G-CSF, granulocyte macrophage colony stimulating factor (GM-CSF), TNF hot shock proteins, and combinations thereof.

17. The method of claim 15 wherein the beneficial agent is a peptide having at least one amino acid selected from the group consisting of cysteine, methionine, tyrosine, tryptophan, phenylalanine, valine, leucine, histidine, glutamic acid, proline, threonine, arginine, and lysine.

18. The method of claim 15 wherein the beneficial agent is a drug selected from the group consisting of epinephrine, theophyllin, risperidone, captopril, chlorpromazine, ergotamine, hydrocortisone, morphine, promethazine, and thiamine.

19. The method of claim 1 further comprising compressing a mixture of the excipient with the beneficial agent to form a pellet.

20. The method of claim 19 further comprising grinding the pellet to form a ground pellet.

21. The method of claim 20 further comprising adding the ground pellet to a viscous gel formulation comprising a bioerodible, biocompatible polymer and a solvent in an amount effective to plasticize the polymer and form a gel therewith.

22. The method of claim 21 wherein the polymer is selected from the group consisting of: polylactides, polyglycolides, polyanhydrides, polyamines, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polyhydroxycellulose, polyphosphoesters, chitin, chitosan, gluronic acid, and copolymers, terpolymers and mixtures thereof.

23. The method of claim 20 further comprising suspending the ground pellet in a bioerodible, biocompatible polymer matrix and encapsulating particles of the ground pellet.

24. The method of claim 23 wherein the matrix comprises a polymer selected from the group consisting of: polylactides, polyglycolides, polyanhydrides, polyamines, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polyhydroxycellulose, polyphosphoesters, chitin, chitosan, gluronic acid, and copolymers, terpolymers and mixtures thereof.

25. The method of claim 1 wherein the excipient has been gamma-irradiated.

* * * * *